United States Patent
Rinsema et al.

(10) Patent No.: US 9,547,094 B2
(45) Date of Patent: Jan. 17, 2017

(54) X-RAY ANALYSIS APPARATUS

(71) Applicant: PANalytical B.V., Almelo (NL)

(72) Inventors: Jeroen Rinsema, Enschede (NL); Mark Alexander Pals, Enschede (NL)

(73) Assignee: PANALYTICAL B.V., Almelo (NL)

( * ) Notice: Subject to any disclaimer, the term of this patent is extended or adjusted under 35 U.S.C. 154(b) by 148 days.

(21) Appl. No.: 14/624,005

(22) Filed: Feb. 17, 2015

(65) Prior Publication Data
US 2015/0234060 A1   Aug. 20, 2015

(30) Foreign Application Priority Data

Feb. 18, 2014   (EP) .................................... 14155632

(51) Int. Cl.
| | | |
|---|---|---|
| G01N 23/223 | (2006.01) | |
| G01T 7/08 | (2006.01) | |
| G01N 23/207 | (2006.01) | |
| B25J 9/00 | (2006.01) | |

(52) U.S. Cl.
CPC ............... G01T 7/08 (2013.01); B25J 9/0093 (2013.01); G01N 23/207 (2013.01); G01N 23/223 (2013.01); Y10S 901/15 (2013.01)

(58) Field of Classification Search
CPC ........ G01T 7/08; B25J 9/0093; G01N 23/207; G01N 23/223; G01N 2223/076
USPC ....................................................... 378/44, 45
See application file for complete search history.

(56) References Cited

U.S. PATENT DOCUMENTS

| | | | | |
|---|---|---|---|---|
| 4,047,029 A | * | 9/1977 | Allport ................. | G01N 23/16 162/263 |
| 5,162,131 A | * | 11/1992 | Rantanen ............... | G01B 15/02 118/665 |
| 2011/0119020 A1 | * | 5/2011 | Key ......................... | G01J 5/00 702/135 |

* cited by examiner

Primary Examiner — Courtney Thomas
(74) Attorney, Agent, or Firm — Leason Ellis LLP

(57) ABSTRACT

X-ray analysis of a primary sample such as a flexible sheet 60 uses apparatus having a primary sample holder such as a material feed-through system 20 for moving the flexible sheet through the apparatus. An X-ray analysis head 6 containing an X-ray source and an X-ray detector is mounted on a robot arm 4. The robot arm moves in three dimensions so that the analysis head can be brought into position to measure the flexible sheet as it is being brought through the apparatus by the material feed-through system.

14 Claims, 2 Drawing Sheets

X-RAY ANALYSIS APPARATUS

FIELD OF INVENTION

The present invention relates to apparatus for measuring a sample such as flexible material using X-ray analysis techniques such as X-ray diffraction or X-ray fluorescence.

BACKGROUND TO THE INVENTION

X-ray analysis is a widely adopted technique for accurately capturing measurement data for materials analysis. X-ray diffraction, XRD or X-ray fluorescence, XRF, are both appropriate in various circumstances. XRF for example can accurately measure can accurately measure elemental composition in a very wide range of concentrations; among others metal, from low concentration impurities (sub-ppm) to high concentrations of major constituents (up to 100%).

Samples for such X-ray analysis may be prepared by a number of methods, for example by compressing powder to a solid sample, or fusing the powder. X-ray analysis can also be carried out on streaming samples, for example powders.

There is however a need for the measurement of a wider variety of samples which need not be flat of or known or fixed shape.

In particular, XRF equipment for measuring flexible sheet material, such as textiles or thin films, of the type that may be wound into rolls, for example, has not previously been available.

Further difficulties may arise with non-flat samples of various shapes.

For the most accurate analysis, both XRF and XRD require calibration and this is a particular issue for XRF. There is accordingly a need for XRD or XRF equipment to measure comparable calibration samples.

SUMMARY OF THE INVENTION

According to a first aspect of the invention, there is provided apparatus for X-ray analysis of a sample, comprising:
  a primary sample holder for holding the sample;
  an X-ray analysis head containing an X-ray source and an X-ray detector, and
  a robot arm mounted on the apparatus, the X-ray analysis head being mounted on the robot arm, the robot arm being arranged to move the X-ray analysis head in three linear dimensions and rotationally so that the analysis head can be brought into position to measure the sample.

The inventors have realised that the provision of rotational motion as well as linear motion allows full flexibility to approach measure or scan surfaces that are not precisely located or parallel to a predetermined direction. In particular, the apparatus can deal with a flexible sheet which has a thickness that varies or an unusual shape. In this regard, it should be noted that very precise positioning of the measurement head with respect to the substrate is required for accurate measurement and the rotational motion allows the head to be positioned exactly parallel to the sample surface even if the sample has a variable thickness such as being locally tapered or curved.

By mounting the X-ray analysis head on a robot arm, the X-ray analysis head can be brought into place for X-ray analysis even if the sample is not flat.

The sample held by the primary sample holder will be referred to as the primary sample.

Preferably, the primary sample holder is a material feed-through system for moving a flexible sheet through the apparatus. The inventors have realised that a flexible sheet moving through apparatus is not always in the same location to the levels of positional accuracy required for X-ray analysis using XRF or XRD. This may occur, for example, because of a variation in thickness, or location of the sheet across the material feed-through system. Since the material is fed through the system in use it is not possible to ensure a very precise fixed position in the same way as is possible with a fixed sample mounted into X-ray analysis apparatus before measurement.

Further, by using the flexibility of motion achievable with a robot arm it is possible to scan across the flexible sheet.

Further developments of the invention are the subject-matter of the dependent claims.

The robot arm may be a six axis robot arm. Such a robot arm provides sufficient flexibility of motion that the system is adaptable to a wide range of thicknesses, sample types and orientations, as well as being able to move between a sample in the form of a flexible sheet in various positions and any additional samples mounted in different planes and/or locations for example integral reference samples. A six axis system also allows for measurement of a static object placed in the housing with an irregular shape so that the measurement head can be brought into a position parallel to the sample surface at various positions over the sample surface even though the sample surface is irregular.

A fixed sample mounting may be provided. The fixed sample mounting may be in the form of a demountable frame, which may be demounted and removed from the apparatus to mount a sample on the frame, and then remounted in the apparatus.

The fixed sample mounting may be provided at a location in the apparatus such that the X-ray analysis head can be moved by the robot arm to analyse a sample mounted on the fixed sample mounting and then be moved back to measure the primary sample.

A fixed reference sample may be mounted to the fixed sample mounting, whether or not in the form of a frame, to provide a reference sample during use.

The fixed sample mounting may be provided on an inner wall of the housing but not in the same plane as the plane of the primary sample holder By using a robot arm with both three dimensional linear as well as rotational motion it becomes possible to mount the reference sample or other fixed sample on a different inner wall of the housing to the position of the primary sample holder. This reduces the overall volume of the apparatus, saving space.

A distance sensor may be provided on the robot arm and/or X-ray analysis head for measuring the position of the arm for locating the X-ray analysis head during measurement. The distance sensor may measure the position of the arm to the primary sample or an additional sample such as a reference sample and hence achieve appropriate positioning of the primary sample or additional sample to the X-ray analysis head regardless of small changes in position or irregularities in shape of the sample during measurement.

A video camera may be provided on the robot arm and/or X-ray analysis head for locating the X-ray analysis head during measurement.

The X-ray analysis head may be an X-ray fluorescence head and/or an X-ray diffraction head. Note that a single head may provide both functions. Alternatively, the head may be removable and/or replaceable.

In a particularly preferred embodiment the X-ray analysis head is an energy dispersive X-ray fluorescence head, i.e. a head adapted to carry out energy dispersive XRF measurements.

In an alternative, the X-ray analysis head is a wavelength dispersive X-ray fluorescence head.

The material feed-through system may comprise rollers. In particular, the feed-through system may comprise a measurement support pair of rollers for supporting the flexible sheet during measurement, the measurement being made on the part of the flexible sheet between the measurement support pair of rollers.

Additional guide rollers may be provided to guide the flexible sheet through the apparatus.

A labyrinth arrangement of rollers may be provided to permit the flexible sheet to enter and leave the housing while maintaining radiation tightness. Entry and exit rollers may in particular be arranged to avoid a direct straight line path between the inside and outside of the housing.

The apparatus may comprises a housing for containing the robot arm, part of the material feed-through system in particular the part supporting the flexible sheet for measurement such as a measurement support pair of rollers.

An external input roller and output roller outside the housing may also be provided.

In use, a flexible sheet in roll form may be mounted on the external input roller and fed through the material feed-through system to the output roller.

The measurement may be carried out as the flexible sheet is passed along the material feed-through system.

Alternatively, the motion of the flexible sheet may be stopped, measurement performed on part of the flexible sheet in a measurement location, and then the flexible sheet moved along the material feed-through system to bring a new part of the flexible sheet to the measurement location and measurement performed again. This may be repeated until sufficient of the flexible sheet as been measured.

BRIEF DESCRIPTION OF THE DRAWINGS

An example of the invention will now be described with reference to the accompanying diagrams, in which.

The drawings are schematic and not to scale.

DETAILED DESCRIPTION

Figure 1:
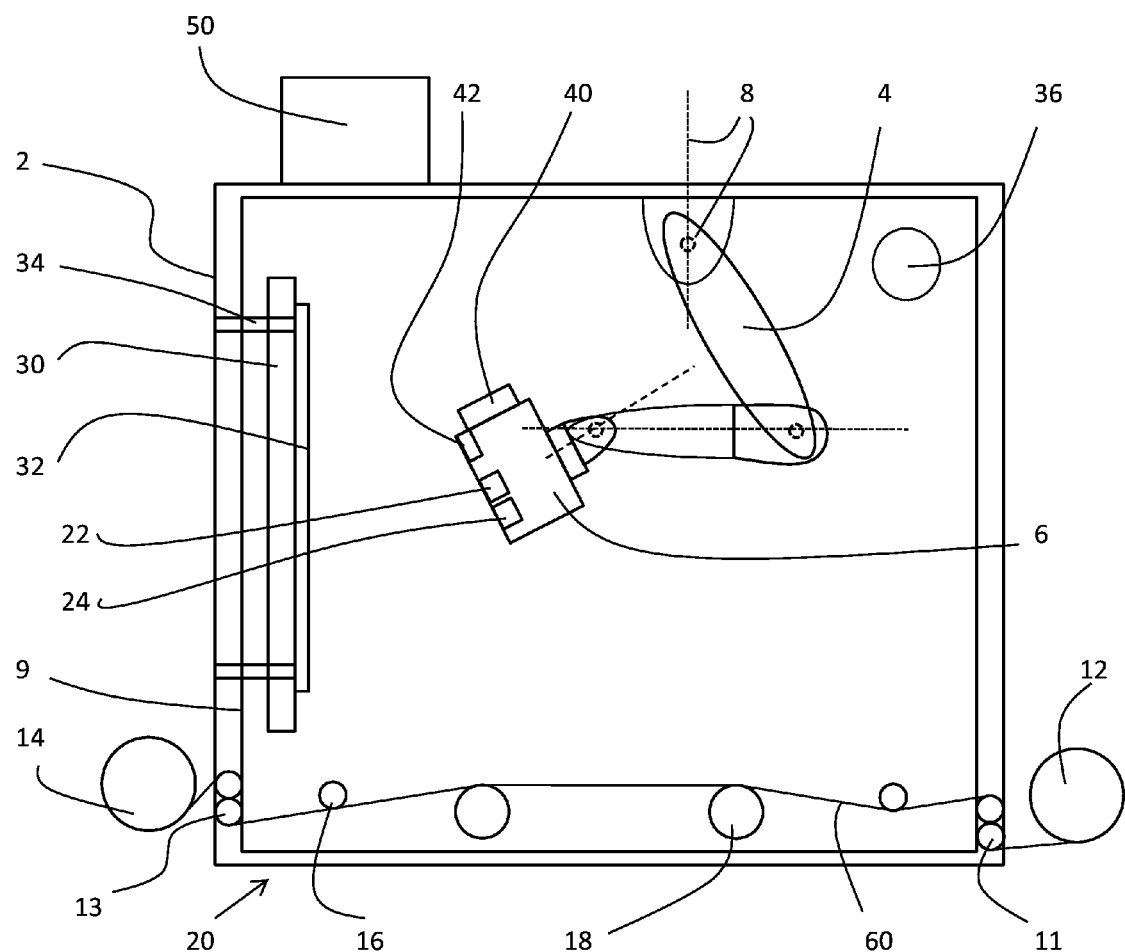
FIG. 1 is a schematic side view of an apparatus according to the invention.

Referring to FIG. 1, X-ray fluorescence apparatus according to the invention has a housing 2, which functions to screen X-rays. The housing 2 has a radiation safety function which reduces external X-ray radiation to safe levels.

The housing 2 supports on the outside of the housing an input roller 12 and an output roller 14. A number of guide rollers 16 are also provided, as well as two measurement rollers 18 whose function will be described later. The rollers 12, 14, 16, 18 make up a material feed-through system 20. Some or all of the rollers 12, 14, 16, 18 may be connected to motors to drive the material through the system. Such rollers will be referred to as driven rollers below. Other rollers may be unpowered and function simply as guide rollers.

Preferably the sheet material is fed-in and fed-out the instrument through a labyrinth construction, thereby obtaining radiation tightness. In order to obtain this part of the cabinet has a double wall. Entry rollers 11 and exit rollers 13 are provided. The sheet material 60 enters the housing 2 at the lower entry roller 11 and passes round the entry rollers 11 in an "S" shape between the lower and upper entry roller 11 and then round the upper entry roller 11 before entering the housing. A similar "S" shaped path is provided at the exit rollers 13. Alternative labyrinth constructions may be provided to likewise maintain radiation tightness with no direct straight line path for X-rays between the inside and outside of the housing in the region of the entry rollers 11 and exit rollers 13.

A robot arm 4 is provided within the housing and an X-ray analysis head 6 is mounted on the distal end of the robot arm 4.

The X-ray analysis head 6 includes an X-ray source 22 and an X-ray detector 24. In the arrangement illustrated, the X-ray detector 24 is an energy sensitive X-ray detector so that the source and detector can carry out energy dispersive XRF measurements in which X-rays are emitted by the source and detected X-rays measured by the X-ray detector.

For X-ray fluorescence measurements the X-ray source may be an X-ray tube typically operating in the 5 to 60 keV range. The source may be broadband without additional optics. Where required, additional optics such as collimating pin-holes or focussing optics can be provided to allow a smaller spot size and hence localised analysis.

Alternative implementations use a wavelength dispersive XRF analysis head.

Alternatively or additionally, the X-ray analysis head 6 may be set up to carry out XRD measurements.

The robot arm 4 is a six-axis robot arm which is capable of six degrees of motion, i.e. rotation about six different axes 8 along the arm. The axes are shown as dotted lines and rings in FIG. 1. This allows a great deal of maneuverability for the X-ray analysis head 6 mounted on the robot arm, and in particular allows for full three-dimensional motion. Accordingly, the X-ray head 6 can be moved across a planar sample in both directions to carry out an x-y scan as well as be moved to different distances from the sample in a controllable and dynamic manner.

A demountable frame 30 is mounted on one inner wall 9 of the housing. The frame is demountable to allow a sample to be mounted on the frame. The frame 30 may then be replaced in the housing so that measurements may be made on the sample mounted on the frame. The frame is spaced from the housing by supports 34.

In particular, in the arrangement shown a reference sample 32 is mounted on the frame 30. The reference sample is used for calibration in use.

A monitor sample 36 is provided mounted inside the housing 2 on a further inner wall 9 of the housing different to the inner wall on which the demountable frame is mounted. This is additional to any reference or other sample that may be mounted on the frame 30. The use of the robot arm allows the mounting of samples not in the same plane as the primary sample holder again making best use of the apparatus and saving space.

The monitor sample is a sample used as a long-term reference for monitoring effects due to X-ray tube aging, for example loss of primary intensity, air pressure fluctuations, which may affect the absorption in air, or system drift in general. This allows for system sensitivity normalisation.

A video camera 40 and a distance sensor 42 are mounted on the robot arm 4. The video camera 40 is mounted adjacent to the X-ray analysis head 6 and the distance sensor 42 is mounted in the X-ray analysis head. Both the video camera 40 and the distance sensor 42 are used for correct alignment and positioning of the X-ray analysis head.

A controller 50 is connected to all of the various components and is used to position the X-ray analysis head by moving the robot arm 4 as well as to get inputs from the video camera 40 and distance sensor 42. The controller also controls the driven rollers 12, 14, 16, 18 of the material feed-through system.

In use, a sample in the form of a roll of a flexible sheet 60 is mounted on the input roller 12. The end of the roll is fed along the guide rollers 16 and measurement rollers 18 to the output roller 14. A suitable reference sample is mounted on the demountable frame.

For example, the sample may be a roll of impregnated textile material 60 that is to be checked for the presence of certain elemental contaminants. Other options include cloth, papers, plastic foils or metal foils.

The user then closes the housing to protect from X-rays and inputs a start command to controller 50.

The controller 50 then causes the system to carry out a measurement method as will now be described. In particular, during measurement, the controller carries out positioning using a feedback loop based on the distance sensor 42 and/or video camera 40 and the distance sensor allows a guarantee of the correct distance.

Firstly, the controller 50 causes the system to move the robot arm 4 so that the X-ray analysis head is a predetermined distance from the reference sample 32. The video camera 40 and distance sensor 42 are used to ensure that the head is a precise distance from the reference sample 32. A calibration measurement is the performed.

The robot arm 4 then moves the X-ray head to a position the same predetermined distance from the part of the flexible sheet 60 between the measurement rollers 18. The measurement is carried out on this part of the flexible sheet by moving the robot arm 4 across this region of the flexible sheet in a measurement pattern. The distance is kept constant even in the face of variations in thickness, or other variation, by monitoring the signal from the distance sensor 42 and adapting the motion of the robot arm 4 to keep the distance constant. The flexibility provided by the head allows the measurement pattern to be adapted to the exact position of the flexible sheet 60 between the measurement rollers 18.

In particular, the inventors have determined that very precise positioning and alignment of the measurement head of the sample is necessary for the most accurate measurements. Preferably, the controller is arranged to control the distance of the head to the sample to at least 10 μm, preferably 5 μm or even 2 μm. It will be appreciated that the thickness of a flexible sheet 60 can easily vary by at least such amounts requiring careful adaptation.

Further, if the thickness varies then the flexible sheet can be locally tapered and in the absence of a rotational motion the surface of the measurement sheet would be non-parallel to the measurement head, which also may reduce measurement accuracy. By translating and rotating the measurement head using the flexibility provided by the robot arm 4 the measurement head can be positioned at a precise predetermined distance from the flexible sheet or other sample to be measured with the measured sample plane perpendicular to the measurement plane (defined by the direction of the central primary beam and the secondary detection direction).

Figure 2:
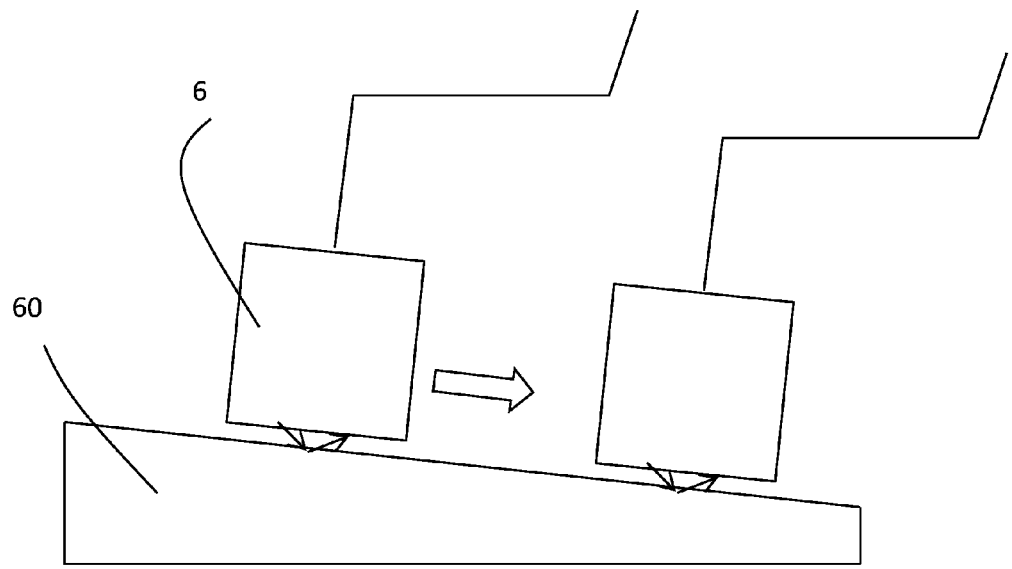
FIG. 2 is a schematic illustration of measurement of a locally tapering sample.

FIG. 2 illustrates the use of the apparatus to measure a sample that is locally tapered illustrating two positions of the measurement head and the feature that the measurement head is rotated to be parallel to the tapered surface.

The driven rollers 12, 14, 16, 18 of the material feed-through system are then driven to bring a new part of the flexible sheet into the measurement region between the measurement rollers 18. The measurement is then carried out again.

This process is then continued until the sheet is measured. The sheet ends up on output roller 14.

Even if the width of the sheet is not constant, the thickness is variable, or the sheet drifts in the longitudinal direction of the measurement rollers 18 during measurement, the adaptability achieved using the robot arm 4 allows for accurate and consistent measurements to be made along substantially all of the flexible sheet.

From time to time, either between measurements, before each flexible sheet is measured or at regular intervals during measurement, the controller 50 causes the robot arm to bring the measurement head 6 to the monitor sample 34 to allow for system sensitivity normalisation.

The reference sample may be used to obtain a reference analysis pattern from which the spectral properties such as the number of peaks, peak position, peak widths and overlap may be determined. This reference pattern may be compared with the patterns obtained from measurement of the flexible sheet 60 for further analysis. Such an approach may be used either XRF or XRD. The use of a reference sample improves the quality and accuracy of measurements made especially for quantitative analysis.

Additional calibration steps can be carried out from time to time by returning the robot arm to the reference sample 32.

In an alternative method of use, the rollers 12, 14, 16, 18 are continually driven so that the sheet 60 is in continual motion and the measurement carried out during this process.

In a further variation, the sample to be measured can be mounted on the reference frame.

Instead of a six-axis arm, a five axis arm which can move the head in three linear directions and two rotational directions may be sufficient for some applications.

Figure 3:
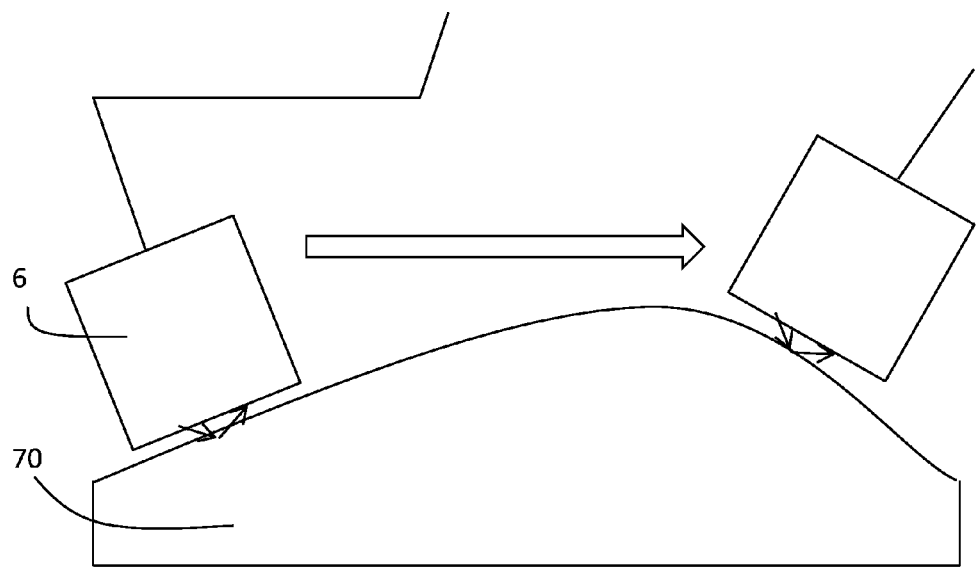
FIG. 3 is a schematic illustration of a measurement of an irregularly shaped sample.

In a further development of the invention, illustrated in FIG. 3, the apparatus may also be used to measure a non-flexible sample 70, either mounted to the frame or alternatively mounted in the location of the measurement rollers 18. The robot arm may be used to carry out measurement over the surface of the sample 70 and is rotated and translated to the correct orientation and predetermined distance as the measurement head traverses the sample.

The invention claimed is:

1. Apparatus for X-ray analysis of a sample comprising:
   a primary sample holder for holding the sample;
   an X-ray analysis head containing an X-ray source and an X-ray detector, and
   a robot arm mounted on the apparatus, the X-ray analysis head being mounted on the robot arm, the robot arm being arranged to move the X-ray analysis head both linearly in three dimensions and rotationally so that the analysis head is brought into position to measure the sample;
   wherein the primary sample holder is a material feed-through system for moving a flexible sheet through the apparatus.

2. Apparatus according to claim 1 wherein the feed-through system comprises a measurement support pair of rollers for supporting the flexible sheet during measurement.

3. Apparatus according to claim 2 further comprising additional guide rollers for guiding the flexible sheet through the apparatus.

4. Apparatus according to claim 1 further comprising a housing for containing the robot arm and part of the material feed-through system for supporting the flexible sheet for measurement.

5. Apparatus according to claim 1 wherein the robot arm is a six-axis robot arm arranged to move the X-ray analysis head in three linear directions and to rotate the X-ray analysis head about three orthogonal axes.

6. Apparatus according to claim 1 further comprising a fixed sample mounting additional to the primary sample holder.

7. Apparatus according to claim 6 wherein the fixed sample mounting is in the form of a demountable frame.

8. Apparatus according to claim 1 further comprising a location sensor on the robot arm and/or X-ray analysis head for measuring the position of the arm for locating the X-ray analysis head during measurement.

9. Apparatus according to claim 8 wherein the location sensor is a distance sensor for measuring the position of the arm to the flexible sheet or to an additional sample.

10. Apparatus according to claim 1 further comprising a video camera mounted on the robot arm and/or X-ray analysis head for locating the X-ray analysis head during measurement.

11. Apparatus according to any claim 1 wherein the X-ray analysis head is an X-ray fluorescence head.

12. Apparatus according to any claim 1 wherein the X-ray analysis head is an X-ray diffraction head.

13. A method of operation of apparatus according to claim 1 including passing a flexible sheet along the material feed-through system and measuring the composition of the flexible sheet using the X-ray analysis head.

14. A method of operation according to claim 13 further comprising measuring the composition of a reference sample using the X-ray analysis head.

* * * * *